US009662595B2

(12) United States Patent
Benevides et al.

(10) Patent No.: US 9,662,595 B2
(45) Date of Patent: May 30, 2017

(54) LIQUID-CHROMATOGRAPHY CONDUIT ASSEMBLIES HAVING HIGH-PRESSURE SEALS (71) Applicant: Waters Technologies Corporation, Milford, MA (US)

(72) Inventors: Christopher C. Benevides, Tiverton, RI (US); Keith Fadgen, Hope Valley, RI (US); Michael Lavallee, Whitinsville, MA (US); Anthony Jeannotte, Foxborough, MA (US)

(73) Assignee: Waters Technologies Corporation, Milford, MA (US)

( * ) Notice: Subject to any disclaimer, the term of this patent is extended or adjusted under 35 U.S.C. 154(b) by 1126 days.

(21) Appl. No.: 13/749,929

(22) Filed: Jan. 25, 2013

(65) Prior Publication Data
US 2013/0134083 A1 May 30, 2013

Related U.S. Application Data (62) Division of application No. 12/811,158, filed as application No. PCT/US2008/086944 on Dec. 16, 2008, now Pat. No. 8,394,275.
(Continued)

(51) Int. Cl.
*B01D 15/10* (2006.01)
*B01D 15/22* (2006.01)
(Continued)

(52) U.S. Cl.
CPC ............ *B01D 15/14* (2013.01); *B01D 15/22* (2013.01); *G01N 30/6026* (2013.01);
(Continued)

(58) Field of Classification Search
CPC ............... G01N 30/60; G01N 30/6004; G01N 30/6026; G01N 30/603; B01D 15/10; B01D 15/22
See application file for complete search history.

(56) References Cited

U.S. PATENT DOCUMENTS

| 3,855,130 A | 12/1974 | Randau et al. |
| 3,920,268 A | 11/1975 | Stewing |

(Continued)

FOREIGN PATENT DOCUMENTS

| EP | 0 134 566 A2 | 3/1985 |
| EP | 0 604 018 A1 | 6/1994 |

(Continued)

OTHER PUBLICATIONS

Extended European Search Report for Application No. 08870285.7, mailed Mar. 27, 2012 (6 pages).
(Continued)

*Primary Examiner* — Katherine Zalasky
(74) *Attorney, Agent, or Firm* — Waters Technologies Corporation (57) ABSTRACT A method for making a liquid-chromatography apparatus includes inserting two inner conduits into an intermediate tube, inserting the intermediate tube into an outer tube, forming a proximal seal between the intermediate tube and at least one of the inner conduits, and forming a distal seal between the intermediate tube and at least one of the inner conduits. A liquid-chromatography apparatus includes an outer tube, an intermediate tube disposed in the outer tube, two inner conduits disposed in the intermediate tube, a proximal seal between the intermediate tube and at least one of the inner conduits, and a distal seal between the intermediate tube and at least one of the inner conduits.

18 Claims, 9 Drawing Sheets

Related U.S. Application Data (60) Provisional application No. 61/018,527, filed on Jan. 2, 2008.

(51) Int. Cl.
*G01N 30/60* (2006.01)
*B01D 15/14* (2006.01)
*B01D 15/26* (2006.01)

(52) U.S. Cl.
CPC ....... *G01N 30/6039* (2013.01); *G01N 30/603* (2013.01); *G01N 30/6004* (2013.01); *Y10T 29/49826* (2015.01)

(56) References Cited

U.S. PATENT DOCUMENTS

| | | | |
|---|---|---|---|
| 4,151,253 A | 4/1979 | Waggoner et al. | |
| 4,207,188 A | 6/1980 | Tsuda et al. | |
| 4,280,905 A | 7/1981 | Gunkel et al. | |
| 4,619,473 A | 10/1986 | Someya | |
| 4,636,316 A | 1/1987 | Harris et al. | |
| 4,842,305 A | 6/1989 | Kistenich et al. | |
| 4,923,226 A * | 5/1990 | Bartholomew | F16L 33/225 285/242 |
| 4,968,421 A | 11/1990 | Spacek et al. | |
| 5,160,178 A * | 11/1992 | Iwabuchi | F16L 19/025 285/328 |
| 5,194,915 A | 3/1993 | Gilby | |
| 5,244,619 A | 9/1993 | Burnham | |
| 5,472,598 A | 12/1995 | Schick | |
| 5,482,628 A | 1/1996 | Schick | |
| 5,540,464 A * | 7/1996 | Picha | G01N 30/6039 210/198.2 |
| 5,601,785 A * | 2/1997 | Higdon | G01N 30/6039 210/198.2 |
| 5,650,846 A | 7/1997 | Yin et al. | |
| 5,651,885 A | 7/1997 | Schick | |
| 5,736,036 A | 4/1998 | Upchurch et al. | |
| 6,068,767 A * | 5/2000 | Garguilo | B01D 15/22 204/455 |
| 6,113,998 A | 9/2000 | Aizawa et al. | |
| 6,199,921 B1 | 3/2001 | Cassel et al. | |
| 6,783,673 B2 | 8/2004 | Horsman et al. | |
| 7,681,926 B2 * | 3/2010 | Valaskovic | G02B 6/3809 285/124.5 |
| 8,394,275 B2 | 3/2013 | Benevides et al. | |
| 2002/0179513 A1 * | 12/2002 | Willis | G01N 30/08 210/198.2 |
| 2004/0080744 A1 | 4/2004 | Hobbs | |
| 2005/0077222 A1 * | 4/2005 | Dawes | G01N 30/6026 210/198.2 |
| 2006/0243651 A1 | 11/2006 | Ricker | |
| 2007/0068872 A1 * | 3/2007 | Gerhardt | B01L 3/565 210/656 |
| 2009/0152108 A1 | 6/2009 | Huttl et al. | |
| 2011/0278214 A1 | 11/2011 | Benevides et al. | |

FOREIGN PATENT DOCUMENTS

| | | |
|---|---|---|
| JP | 07-306191 A | 11/1995 |
| WO | 82/01578 A1 | 5/1982 |
| WO | 95/05229 A1 | 2/1995 |
| WO | 2006/130408 A2 | 12/2006 |
| WO | 2007/038003 A1 | 4/2007 |

OTHER PUBLICATIONS

International Search Report and Written Opinion for Application No. PCT/US2008/086944, mailed Feb. 25, 2009 (9 pages).

Japanese Search Report for Application No. 2010-541478, issued Jan. 31, 2013 (26 pages).

Japanese Office Action for Application No. 2010-541478, dated Feb. 5, 2013 (4 pages).

U.S. Appl. No. 12/811,158, filed Aug. 11, 2010, Liquid-Chromatogoraphy Conduit Assemblies Having High-Pressure Seals.

\* cited by examiner

FIG. 8B

# LIQUID-CHROMATOGRAPHY CONDUIT ASSEMBLIES HAVING HIGH-PRESSURE SEALS

CROSS REFERENCE TO RELATED APPLICATIONS

This application is a divisional of application Ser. No. 12/811,158, filed on Aug. 11, 2010, which is the National Stage of International Application No. PCT/US2008/086944, filed Dec. 16, 2008, which claims priority to U.S. Provisional Application No. 61/018,527, filed Jan. 2, 2008. The entire contents of these applications are incorporated herein by reference.

TECHNICAL FIELD

The invention generally relates to chromatography apparatus that operate at high pressure. More particularly, the invention relates to conduit assemblies that include conduits joined in a manner that provides high-pressure seals.

BACKGROUND INFORMATION

Various instruments utilize conduits, such as tubes for transportation of process fluids and sample compounds and/or for separation of sample compounds, and optical fibers to transport light. For example, chemical-analysis instruments that utilize liquid chromatography (LC), capillary electrophoresis (CE) or capillary electro-chromatography (CEC) perform separation of sample compounds as the sample passes through a column, or concentrate a sample in a trap column before delivery of the concentrated sample to a separation column. Such instruments include plumbing, such as tubes and connectors, that transport a variety of materials, such as solvents and sample compounds.

In addition to tubing, liquid-chromatography apparatus typically include, for example, reservoirs, pumps, filters, check valves, sample-injection valves, and sample-compound detectors. Typically, solvents are stored in reservoirs and delivered as required via reciprocating-cylinder based pumps. Sample materials are often injected via syringe-type pumps.

In some cases, separation columns include one or more electrodes to permit application of a voltage to a sample-containing fluid passing through and/or exiting from the conduit. CEC, for example, utilizes an electro-osmotic flow (EOF) to propel a mobile phase through a chromatographic column. In contrast, high-performance liquid chromatography (HPLC) relies on pressure to propel a fluid through a column.

Suitable tubing withstands pressures encountered during fabrication and use, is reliable through repeated use, and has physical and chemical compatibility with process and sample compounds. Generally, a tubing material should not corrode or leach, and sample compounds should not adhere to the tube (unless required for a separation process.)

For HPLC and higher-pressure applications, tubing is typically made from stainless steel or fused silica to provide suitable strength and cleanliness. Such tubing is typically joined to other components via stainless steel connectors.

Stainless steel, however, has disadvantages in some applications due to its biocompatibility limits in comparison to some other materials; some organic molecules tend to adhere to the inner walls of steel tubing, and components of a steel alloy at times leach into fluid passing through the tubing. Organic molecules generally are less likely to stick to fused silica or suitable polymeric materials than to steel. Fused silica tubing, however, is vulnerable to fracturing while polymeric materials generally have relatively poor strength.

Typically, tubing must also be compatible with connectors that provide fluidic connections to other components of an instrument. Problems associated with the design and use of connector fittings are particularly difficult for high-pressure fabrication and operation. For example, pressures in the range of 1,000-5,000 pounds per square inch (psi) or higher are often utilized in liquid chromatography, and must be accommodated without undesirable amounts of leakage. Tubing connections should generally minimize dead volume, a problem that grows worse as dimensions are reduced.

SUMMARY OF THE INVENTION

The invention arises, in part, from the realization that two conduits, in a chromatography-based apparatus, are advantageously joined, when disposed inside one or more tubes, through use of a fluid-tight seal and a stabilizing seal. A fluid-tight seal, proximal to the joint between two conduits, is provided, for example, through use of pressure, while a stabilizing seal, distal to the joint, is provided by adhering the conduits to the tube. Thus, the integrity of an interface at the joint is preserved while providing high-pressure operation and avoiding slippage of the inner conduits during high-pressure use and/or repeated pressure cycling.

Some embodiments of the invention arise from the realization that an assembly that includes a polymer intermediate tube disposed between a relatively rigid outer tube and a relatively rigid and/or brittle inner conduit is well suited to implement the above-mentioned seals.

The invention is well suited, for example, to mate tubes having small and/or different inner diameters. Some embodiments of the invention provide low dead-volume connections between capillaries having different inner diameters and/or reduce the number of fittings required to plumb a chromatography apparatus. The invention is also well suited for fabrication of columns, such as trap columns.

Some implementations include layered tubing that provides the narrow inner dimensions and other benefits of fused-silica capillary plumbing, while also providing the mechanical stability and good connector interface of steel tubing in high-pressure applications.

Accordingly, one embodiment of the invention features a method for making a liquid-chromatography apparatus. The method includes inserting at least two inner conduits into an intermediate tube, inserting the intermediate tube into an outer tube, forming a proximal seal between the intermediate tube and at least one of the inner conduits, and forming a distal seal, between the intermediate tube and at least one of the inner conduits. The inner conduits are disposed such that their facing ends are adjacent to one another, and, in some embodiments, in direct contact. The proximal seal is located near to the facing ends, and the distal seal is located further from the facing ends.

The proximal seal is provided, for example, by deforming the outer tube to press the intermediate tube against the inner conduit. The proximal seal preferably provides a substantially liquid-tight seal between the inner conduit and the intermediate tube.

The distal seal is formed, for example, by causing the intermediate tube to adhere to the inner conduit in one or more regions. For example, local melting and/or softening of the intermediate tube optionally supports formation of the distal seal. The distal seal preferably has a seal area that is larger than a seal area associated with the proximal seal. The distal seal preferably prevents the inner conduit from sliding within the intermediate tube during pressure cycling.

The intermediate and outer tubes are formed respectively, for example, from a polymeric material and a metallic material. The inner conduits, in various implementations are, for example, tubes and/or optical conduits. In some preferred embodiments, two inner conduits are fused silica capillaries of same or different inner diameters.

Another embodiment of the invention features a liquid-chromatography apparatus. The apparatus includes: two inner conduits disposed end-to-end, in contact, to define a low dead-volume interface; an intermediate tube, within which the two inner conduits are disposed; and an outer tube, within which the intermediate tube is disposed. The outer tube is deformed at at least one location proximal to the interface to form a substantially liquid-tight seal area between the inner conduits and the intermediate tube. The intermediate tube is attached to at least one of the two inner conduits at a distal seal area spaced from the interface. In some implementations, the apparatus includes a separation column, and a pump unit configured to deliver a fluid at a pressure of at least about 10,000 psi.

Another embodiment of the invention features a liquid-chromatography apparatus. The apparatus includes a light-based detector, which includes: a liner tube and an optical conduit disposed end-to-end to define an interface; an intermediate tube that is attached to at least one of liner tube and the optical conduit at a distal seal area spaced from the interface; an outer tube, that is deformed at at least one location proximal to the interface to form a substantially liquid-tight seal area between the liner tube and/or the optical conduit and the intermediate tube; a light source to deliver light to a liquid in the liner tube, via the optical conduit; and a sensor to receive light exiting from the liquid in the liner tube.

Some embodiments are compatible with commonly available metallic-based high-pressure connectors. Some of these embodiments are fabricated from standard stainless steel or titanium tubing that is suitable for operation at relatively high pressures. Thus, as one example, a relatively high-pressure compatible conduit assembly is constructed at a relatively low cost from readily available components and integrated with other components of a nano-flow instrument by utilizing standard high-pressure connectors.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 8b is a side view of the fluidic-interface portion of the flow-cell assembly of FIG. 8a.

DESCRIPTION

The phrases "chromatographic system," "chromatographic module," "chromatographic instrument," and the like herein refer to equipment used to perform chemical separations. Such equipment exists as a portion of an instrument that includes other components or is a standalone unit. Chromatographic equipment typically moves fluids under pressure and/or electrical forces.

Depending on context, the description provided herein of some illustrative embodiments of the invention interchangeably uses the words "tube," "conduit," and/or "pipe." Depending on context, the word "capillary" refers to fused-silica tubes and/or refers to tubes having a relatively narrow inner diameter. Tubes and pipes define an interior passageway(s), herein also referred to interchangeably as a lumen, bore, or channel. Interior and exterior surfaces of a tube have a circular or other suitable cross section (such as a rectangular or square cross section.) The word "column" herein refers to a tube assembly that is used for separation or other processing of compounds in a sample, or is used to propel fluids in an electrokinetic pump.

The word "biocompatiblity" herein relates to the tendency of some organic materials to adhere to a particular tube material, as would be understood by one of ordinary skill. For example, fused silica is generally considered to be more biocompatible than is steel because organic molecules are typically less likely to adhere to fused silica than to a steel alloy.

The terms "nano-flow" and "nanoflow" are used herein to refer to fluid flow rates of less than about 100 µL/min. Nano-flow rates are useful, for example, in some applications of chromatography performed at pressures of 1,000 psi or greater, and at even higher pressures, such as 10,000 psi or greater.

Some embodiments of the invention involve apparatus that include both chromatographic and mass-spectrometric components. In some of these embodiments, a chromatographic component is placed in fluid communication with a mass-spectrometric component through use of an appropriate interface, such as an electrospray-ionization interface, as known to one of ordinary skill. Some appropriate interfaces at times create or maintain separated materials in an ionic form and typically place a stream of fluid containing the ions into an atmosphere where the stream is vaporized and the ions are received in an orifice for mass-spectrometric analyses.

Figure 1:
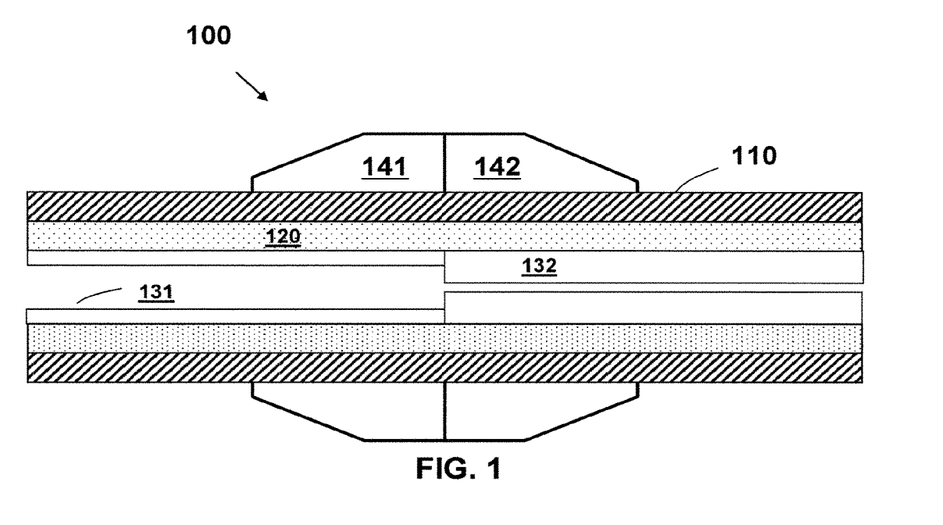
FIG. 1 is a cross-sectional diagram of a tubing joint, in accordance with one embodiment of the invention.

FIG. 1 is a cross-sectional diagram of a conduit assembly 100, which includes at least one high-pressure seal and is a portion of a liquid chromatography-based apparatus, in accordance with one embodiment of the invention. The assembly 100 includes an outer tube 110, an intermediate tube 120 and two inner conduits 131, 132. The inner conduits 131, 132 are disposed end-to-end within the intermediate tube 120, preferably in contact, to define a low dead-volume interface. The intermediate tube 120 is disposed within the outer tube 110. Two optional fittings 141, 142, such as metal ferrules, are disposed around the outer tube 110 adjacent to the interface between the two inner conduits 131, 132. As described in more detail, below, the assembly 100 includes, between the intermediate tube 120 and at least one of the conduits 131, 132, at least one liquid-tight seal and at least one stabilizing seal. In some alternative embodiments, a frit is disposed between the inner conduits 131, 132.

In various embodiments, the intermediate tube 120 is formed from a polymeric material. In some cases, the material is selected for its ability to form a melt bond to the outer tube and/or for its biocompatibility. In some alternative embodiments, portions of a polymeric intermediate tube or other polymeric tubes are directly exposed to a liquid in an assembly. In some embodiments, an intermediate tube is at least partially formed of any suitable meltable polymer, including known thermoplastic polymers.

The polyaryl-ether-ketones, for example, provide one class of thermoplastic polymers that also has good biocompatibility. One of the suitable polymeric materials of this class is polyether-ether-ketone, such as PEEK polymer (available from Victrex PLC, Lancashire, United Kingdom.)

Some embodiments utilize other polymers, for example, fluoropolymers such as polytetrafluorothylene (available as TEFLON® polymer from Dupont Engineering Polymers, Newark, Delware), chlorotetrafluoroethylene, polychlorotrifluoroethylene (available as NEOFLON® PCTFE fluoropolymer from Fluorotherm Polymers, Inc., Fairfield, N.J.), and modified copolymer fluoropolymers (for example, a modified copolymer of tetrafluoroethylene and ethylene available as DUPONT TEFZEL® fluoropolymer, which is resistant to concentrated nitric acid or sulfuric acid), and other polymers, such as polyimide (available as DUPONT VESPEL® polyimide.) TEFLON® AF amorphous fluoropolymer is particularly well suited for tubes that must conduct both a liquid and light through a lumen in the tube (see, for example, embodiments described below with reference to FIGS. 7, 8a and 8b.)

The intermediate tube 120 is optionally formed of a composite material. For example, the tube 120 is formed of a mixture of a polymer, such as polyether-ether-ketone, and about 5% by weight of glass, fiberglass, carbon, and/or or other particles and/or fibers.

The material of the outer tube 110 is any suitable material, including known materials, that provides, for example, a sufficient level of mechanical strength to support fabrication and/or operating conditions. Steel and titanium alloys, for example, are suitable deformable materials, which also have high yield strength, if required. Moreover, some embodiments utilize standard tubing known to those having ordinary skill in the high-pressure chromatographic arts. One suitable standard tubing is 1/16 inch outer diameter ("OD") 316 alloy stainless steel tubing. The inner diameters ("ID") of the steel tubing are selected as desired from, for example, standard available IDs. Standard IDs are available as small as approximately 4 mil (about 100 μm.) The inner conduits 131, 132, in some implementations, are fused-silica capillaries.

The OD of the intermediate tube 120 is optionally selected to provide a slidable fit within the outer tube 110. An ID of the intermediate tube 120 is selected as desired. For example, an ID can be selected to be as small as approximately 2 mil (about 50 μm) or less.

As noted above, the assembly 100 has one or more liquid-tight seals, proximal to the interface. The seals exist between the intermediate tube 120 and one or both of the inner conduits 131, 132. The seals preferably provide liquid-tightness at pressures of 1,000 psi or greater, or 5,000 psi or greater, or, more preferably, at 10,000 to 15,000 psi or greater.

In this example embodiment, liquid-tight seals are formed by crimping the fittings 141, 142 to deform the outer tube 110 and indirectly apply pressure between the intermediate tube 120 and the inner conduits 131, 132. The deformation of the outer tube 110 preferably continuously encircles the intermediate tube 120 to ensure the liquid tightness of the associated seal. The deformable material of the outer tube 110 is preferably a metal such as a steel or titanium alloy. The outer tube 110 material optionally provides a greater yield strength than the material of the intermediate tube 120.

The assembly 100 has at least one stabilizing seal—located distal to the interface relative to the proximal seal—between the intermediate tube 120 and either or both of the inner conduits 131, 132. The stabilizing seal preferably prevents the inner conduits 131, 132 from displacing or sliding within the intermediate tube 120 in response to application of pressure. The distal seal is desirably associated with a larger seal area than that associated with the proximal seal, to provide mechanical stability. Thus, some embodiments of the invention provide liquid-tightness close to a conduit interface through use of a relatively small area mechanical seal, and provide mechanical stability through use of a larger-area seal further from the interface.

The distal seal is formed via any suitable process, including known processes. For example, as described in more detail, below, the intermediate tube 120 is optionally formed of a polymeric material, and heat is applied to the outer tube 110 in the vicinity of the desired location of the distal seal. The intermediate tube 120 melts, locally, and adheres, upon cooling, to one of the inner conduits 131, 132. Preferably, heating is controlled, for example, via distance from the interface, to protect the interface from damage, for example, from melting in the vicinity of the interface.

Various alternative embodiments include one, two or more liquid-tight seals and one, two or more stabilizing seals, in assemblies that include two or more inner conduits. The particular configuration and materials of the conduits 110, 120, 131, 132 are selected to suit a particular application. Some additional illustrative examples are described below. One having ordinary skill in the chromatographic arts will recognize, however, that a broader range of applications is amenable to application of the invention.

Various embodiments of the invention mate various types of inner conduits. For example, as illustrated in FIG. 1, the inner conduits optionally are two tubes having different ID. In other embodiments, an inner tube is mated to a conduit having no lumen, such as an optical fiber. Many of these embodiments, as described above, provide a secure interface that is both fluid-tight and stable under the influence of repeated high-pressure cycling.

Figure 2A:
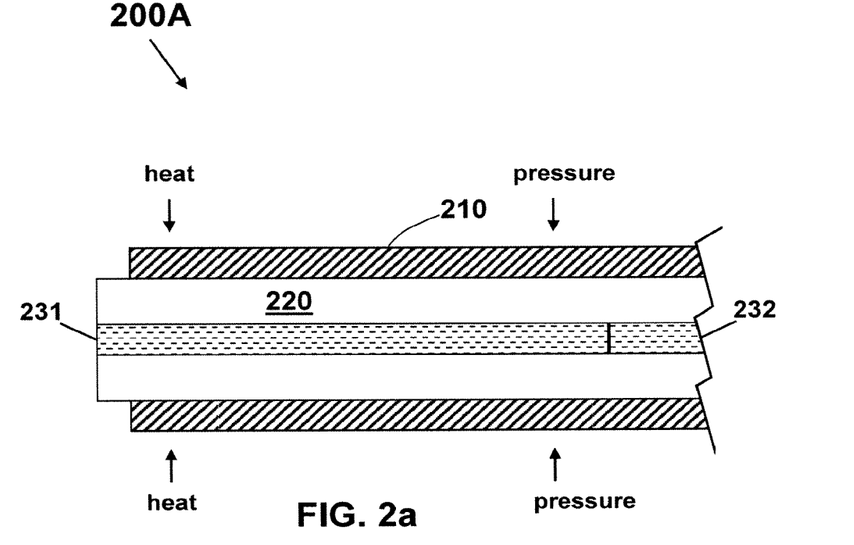
FIG. 2a is a cross-sectional diagram of tubing at an intermediate stage of fabrication, in accordance with one embodiment of the invention.
Figure 2B:
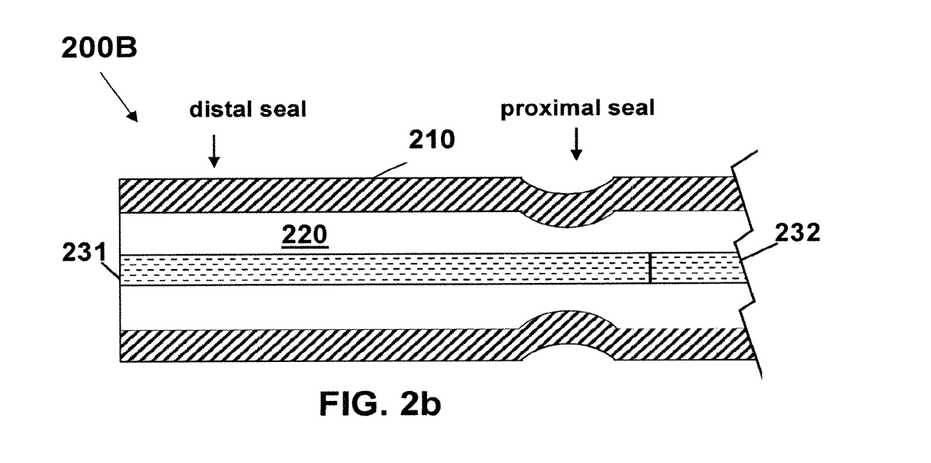
FIG. 2b is a cross-sectional diagram of the tubing of FIG. 2a at a later stage of fabrication.

Now referring to FIGS. 2a and 2b, one method of fabricating an assembly, such as the assembly 100, is described in more detail. FIGS. 2a and 2b illustrate cross-sectional views of an assembly as it appears before seal formation (200A) and after completion (200B). The assembly 200A includes a steel outer tube 210, a polymeric intermediate tube 120 and two inner conduits 231, 232. The inner conduits 231, 232 are disposed in direct contact within the intermediate conduit 220. The inner conduits 231, 232 are illustrated without lumens, though either or both conduit 231, 232 optionally has a lumen, as desired for a particular application.

Near to the interface between the inner conduits 231, 232 (or at the interface, in alternative embodiments) the outer tube 210 is deformed via application of pressure (with or without use of one or more fittings, such as the fittings 141, 142 illustrated in FIG. 1.) The locally deformed outer tube 210 applies a ring of pressure between the intermediate tube 220 and the neighboring conduit (conduit 231 and/or conduit 232; as illustrated, the conduit 231.) The outer tube 210 also constricts flow of the polymeric material of the intermediate tube 220, in response to the local deformation. This constriction helps to maintain a desired level and localization of pressure between the intermediate tube 220 and inner conduit 231 by limiting the ability of polymeric material to flow away from the location of constriction.

As desired, additional pressure-based seals are formed, for example, adjacent to the opposite side of the interface and/or at one or more locations further from the interface. Such additional seals optionally provide redundancy for fluid tightness and/or support against movement of the conduits 231, 232 along the intermediate tube 220. In some cases, the above-described fluid-tight seal, near or at the interface, is preferably supported with additional seals.

The distal seal preferably supports the fluid-tight seal by providing additional mechanical stability for the associated conduit 231, 232 against sliding movement with the intermediate tube 220. Any suitable process is used to form the distal seal, including known processes. For example, the seal is formed via friction, an adhesive material, and/or other mechanisms.

More generally, an assembly optionally includes one, two, or more stabilizing seals, to either or both sides of an interface. Multiple stabilizing and fluidic seals are optionally disposed in any number and any positional order, as desired. The seals are optionally formed in any sequence and/or simultaneously.

In the present example, the distal seal is formed by using heat to adhere the inner conduit 231 to the intermediate tube 220. One or more distal seals are optionally formed, for one or both of the inner conduits 231, 232. As described in more detail below, the outer tube is heated to cause local softening and/or melting of the polymeric material of the intermediate tube. Heating is controlled to avoid damage to the polymer in the vicinity of the interface. In some cases, heat is applied at a location that is at least approximately 10 mm distal to the interface.

During heating, a gas or liquid is optionally directed through a lumen of the conduit 231 to help control the temperature profile of the heated zone. The fluid extracts heat from the interior surface of the inner tube 231 during melting of a portion of the intermediate tube 220.

The intermediate tube 220 is heated in any suitable manner. In one embodiment, the intermediate tube 220 is heated indirectly by heating an adjacent portion of the outer tube 210. For example, the intermediate tube 220 is heated by heating the outer tube 210 sufficiently to raise the temperature of portions of the intermediate tube 220 to at least a melting point temperature.

Heat is directed at the outer tube in any suitable manner, including known heating methods. For example, the assembly 200A, or portions of the assembly 200A, are placed in one or more ovens or in cavities of heatable blocks of aluminum or steel. Such blocks are heated by, for example, resistive heaters or a heated platen. Other options for heating, such as induction heating, are available and any suitable method may be used. Various embodiments utilize any method of heat transfer that provides the desired bonding temperature and environment.

The portion of the intermediate tube 220 that is melted has its temperature profile controlled as desired. For example, the temperature is raised gradually to a desired temperature over a period of seconds or minutes or hours. Alternatively, the portion of the intermediate tube 220 is melted nearly instantaneously. In some embodiments, a suitable temperature profile that supports a good bond is empirically or theoretically determined.

In some embodiments, heating over a period of several minutes is helpful to obtain a good bond. It is desirable in some cases to controllably heat and melt the portion of the intermediate tube to obtain repeatable results and to avoid incorporation of bubbles or voids within a bonded region.

In some cases, it is undesirable to overheat the polymeric material of the intermediate tube when thermal breakdown or decomposition is possible. One embodiment utilizes a non-oxidizing atmosphere during heating.

After heating, the assembly 200B is either passively or actively cooled to ambient temperature. Cooling is accelerated by, for example, any suitable method that maintains the chemical and structural integrity of the bond and components.

The remaining description, below, is directed primarily to the use of a polyether-ether-ketone intermediate tube. One having ordinary skill will understand, however, that principles of the invention are applicable to a broader range of materials and processing conditions.

Localized melting, in one illustrative case, is obtained by heating portions of the intermediate tube to a temperature somewhat above the melting point temperature. In one embodiment, for example, the polyether-ether-ketone portion is heated to a temperature of between about 385° C. to about 405° C. The polymer is heated at the desired temperature for a period of time of about 1 to about 3 minutes, although the invention is not limited to such. It is often desirable to heat neighboring portions of an intermediate tube and an inner conduit to a similar or same temperature during melting to obtain a good bond.

In one example, a completed assembly includes an intermediate tube and an outer tube of the following dimensions and composition. The outer tube is formed of drawn 316 stainless steel and the intermediate tube is formed of extruded polyether-ether-ketone. The intermediate tube has an ID of 2 mil (50 μm) or 2.5 mil (60 μm). The outer tube has an outer diameter of 1/16 inch, and has an ID selected to be compatible with the OD of the intermediate tube. The word "compatible" is herein used to mean that the intermediate tube can be inserted into the outer tube. Preferably, during insertion, the intermediate tube is not damaged and there is some contact around the circumference of the intermediate tube, i.e., there is a minimal gap between the inner and outer tubes. One having ordinary skill will understand this example is merely illustrative and non-limiting.

In view of the description provided herein of illustrative embodiments fabricated from inner, intermediate and/or outer tubes, numerous alternative assembly configurations will be apparent to one having ordinary skill in the chemical separation arts. Optionally, more than one intermediate tube and/or more than one outer tube are utilized to fabricate assemblies. For example, some embodiments entail two or more outer and/or intermediate tubes, disposed in a row and/or disposed within one another. For example, in one embodiment, multiple intermediate tubes are inserted serially, one after another, into an outer tube. In another embodiment, multiple intermediate tubes are disposed side-by-side in parallel. Portions of one or more of the inserted intermediate tubes are then melted to bond the tubes to each other and/or to inner conduits within one or more of the intermediates tubes.

In another embodiment, intermediate tubes are inserted within one another. In still another embodiment, outer tubes are inserted within one another. Thus, some embodiments include more than two concentrically disposed tubes. Moreover, conduits optionally include inner and/or outer coating (s). For example, fused-silica capillaries optionally include a polyimide coating for protection against breakage.

Figure 3:
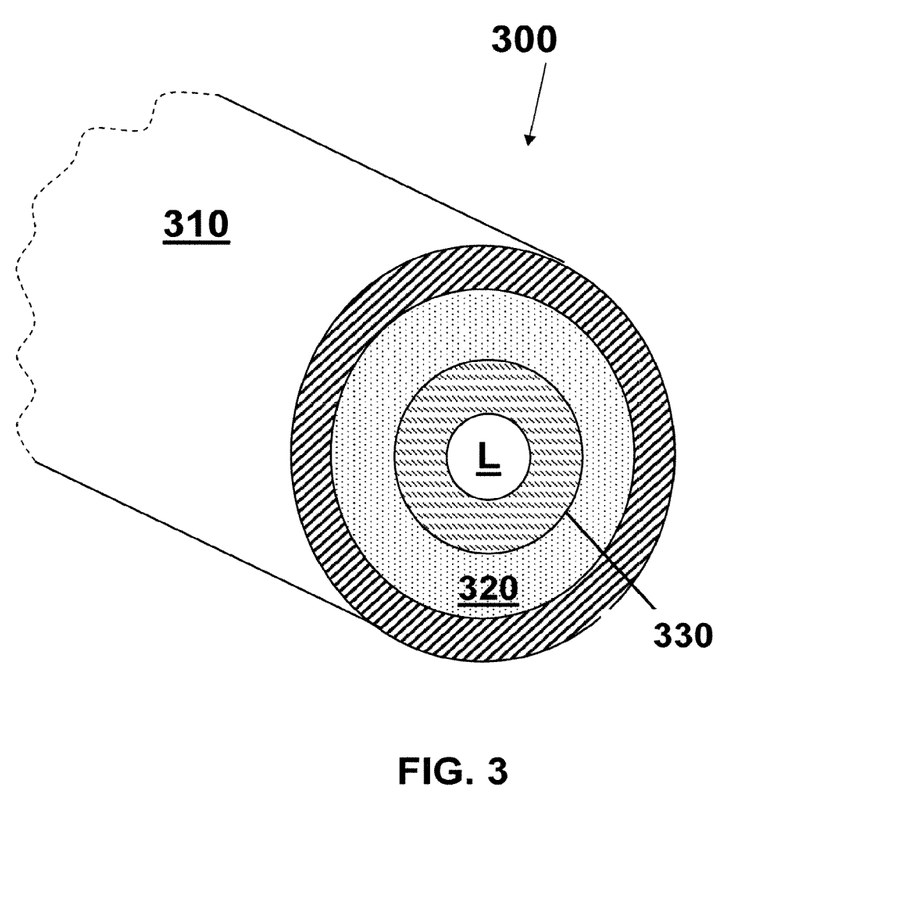
FIG. 3 is an angled end view of a tubing assembly, in accordance with one embodiment of the invention.

Referring next to FIG. 3, one or both ends of an assembly, such as the assembly 200B, are optionally cut and/or polished for compatibility with other components of an apparatus. For example, as illustrated FIG. 2b, at least one end of the assembly 200B has been polished to a smooth finish. In alternative embodiments of the invention, one or both ends of an assembly are trimmed and/or otherwise shaped as desired for compatibility with other components of an chemical apparatus. Trimming in support of compatibility with conduit connectors is described below, with reference to FIG. 5.

FIG. 3 illustrates a three-dimensional angled end view of a polished end of an assembly 300, in accordance with another illustrative embodiment of the invention. The assembly 300 is similar in structure and appearance to the smoothed end of the assembly 200B of FIG. 2b. The assembly 300 includes an outer tube 310, an intermediate tube 320 and an liner tube 330 that has a lumen L.

The outer, intermediate, and liner tubes 310, 320 330 are each fabricated in any desired dimensions in any suitable manner from any suitable materials, including known fabrication methods and materials. For example, the outer tube 310 and the intermediate tube 320 optionally have some or all of the compositional and dimensional features, respectively, of the outer tube 210 and the intermediate tube 220 described above.

The end shape of the assembly 300 supports use of suitable connectors, such as known connectors, that mate with relatively large diameter metallic tubing to obtain substantially fluid-tight and durable plumbing connections at pressures of up to 1,000 psi, or up to 5,000 psi, or up to 10,000 psi, or greater. Some suitable connectors are described below with reference to FIG. 5.

Although not required, standard lengths of commercially available tubing are amenable for use in assemblies and apparatus of the invention. Completed assemblies optionally have straight and/or curved portions, or other desired configurations. For example, in one embodiment a length of metallic tubing is bent at one or more sections to provide a desired configuration for use in a particular analytical instrument. An intermediate tube is inserted before or after bending of the outer tube. Alternatively, an outer tube is manufactured with a non-straight configuration so that bending is not required.

Figure 4A:
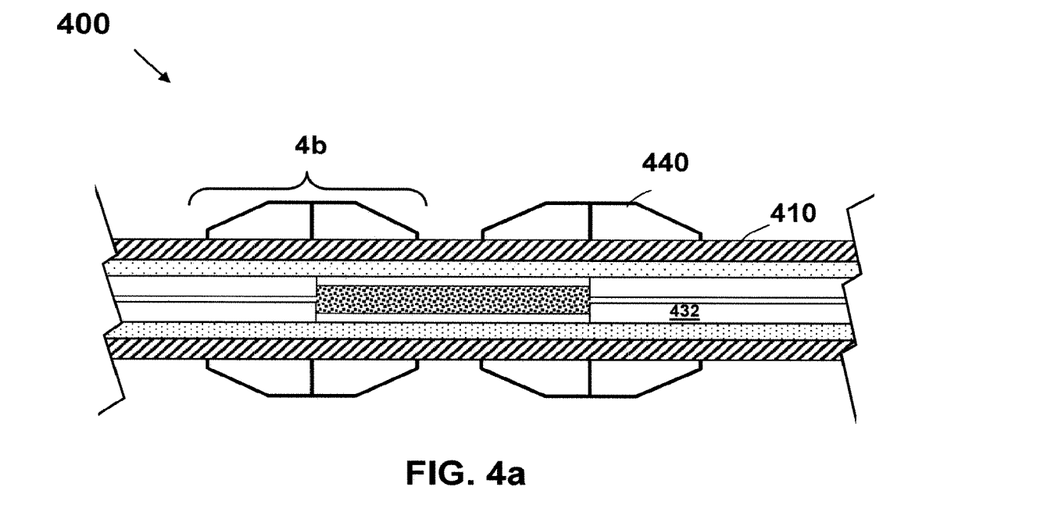
FIG. 4a is a cross-sectional diagram of a packed column, in accordance with one embodiment of the invention.
Figure 4B:
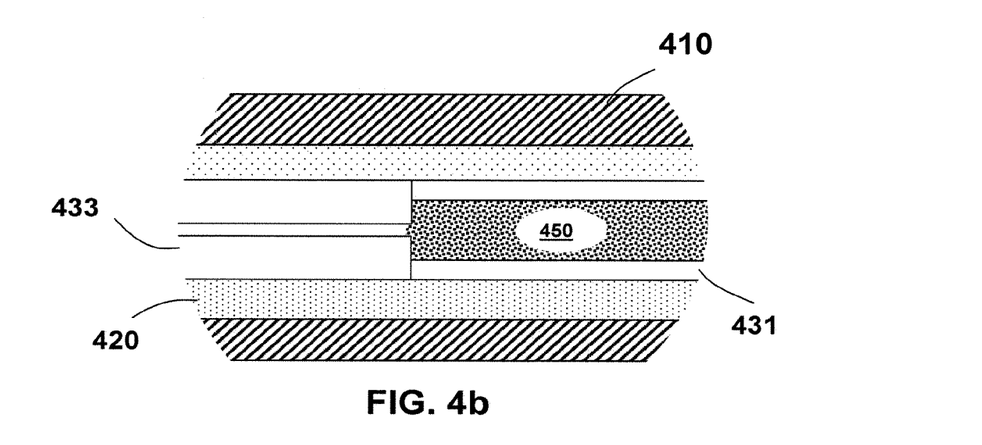
FIG. 4b is an enlarged portion of the cross-sectional diagram of FIG. 4a, centered on an interface between two liner tubes of different inner diameters.

Various embodiments of the invention implement the above-described principles to realize a variety of genres of assemblies. For example, FIG. 4a is a cross-sectional diagram of a packed-column assembly 400, in accordance with another embodiment of the invention. FIG. 4b is an enlarged cross-sectional diagram of a portion of the assembly 400 (see reference 4b in FIG. 4a.)

The assembly 400 includes an outer tube 410, an intermediate tube 420 and three liner tubes 431, 432, 433. The liner tubes 431, 432, 433 are disposed in contact at two low dead-volume interfaces. The central liner tube 431 of the liner tubes 431, 432, 433 has a larger ID than the other liner tubes 432, 433. A packing material 450 fills the interior of the central tube 431. The intermediate tube 420 is disposed within the outer tube 410. Optional fittings 440, such as metal ferrules, are disposed around the outer tube 410 adjacent to the interfaces.

The assembly 400 is suitable for use as, for example, a trap column or a separation column. The dimensions and packing material are chosen for a particular application, as will be understood by one having ordinary skill in the chromatographic arts.

In another, more detailed, example, a trap-column assembly that uses two liner tube provides a relatively low-cost high-pressure trap column for a LC apparatus. The liner tubes are fused silica capillaries having an OD of 360 μm, an ID of 40 μm for a packed liner tube and an ID of 180 μm for the other liner tube.

This example trap-column assembly is fabricated by packing a length of 180 μm ID tubing, and cutting the packed tubing to a length of 20 mm. An intermediate tube formed of polyether-ether-ketone polymer (length about 1.75", ID of about 0.0155", OD about 0.025") is inserted into an annealed steel tube (length about 1.50", ID of about 0.026", OD about 0.0332".)

The intermediate tube is inserted into the steel tube until flush with one end of the steel tube. The packed 20 mm tube is inserted into the flush end of the intermediate tube. One of the 40 μm ID tubes is inserted into the opposite end of the intermediate tube until the 40 μm ID tube makes contact with the packed 180 μm ID tube.

The unfinished assembly is heated in two locations for 20 seconds each with a heat gun (to a temperature of approximately 450° C.) One heated location is near the mid-point of the packed 20 mm tube. The second location is along the 40 μm ID tube about 10 mm away from the interface between the two liner tubes. Heating is controlled to avoid flowing of melted polymer into the joint at the interface. Ferrules are disposed about the outer tube, as illustrated in FIG. 4a, and compressed to permanently deform them into the assembly.

The flush end of the assembly is polished and cleaned. Optionally, the flush end is then fitted to a component, such as a splitter (see, for example, FIG. 6 and related description.) Thus, in this example embodiment, the outlet of the trap column optionally is directly attached to a fitting of an apparatus, thus reducing the number of tubes, houses and fittings that might otherwise be required to join two silica capillaries or connect a trap column.

Some embodiments of the invention that include packed tubes utilize chemical frits to help retain a packing material in a tube without substantial increase of dead volume. Any suitable chemical frit process is optionally used, including known processes. As one example, a chemical frit is formed from a siloxane-based thermoset polymer, for example, poly(dimethyl siloxane) ("PDMS".)

For example, packing material is added to a PDMS-based solution. A tube is dipped into the solution, placed under vacuum and removed from the vacuum to air dry. The fritted end of the tube is then dipped in a PDMS-based solution without packing material, so the solution can wick into the unfinished frit. The wetted material is allowed to dry and then heated to a temperature of approximately 110° C. to cure the PDMS solution. The fritted end of the tube is optionally then heated to sinter the packing material. Upon completion of the frit, the remaining unpacked space of the tube may be filled with packing material.

Assemblies according to many embodiments of the invention are well suited for use with tubing connectors, such as standard connectors known to those having ordinary skill in the separation arts. It should also be understood that the above- and below-described and illustrated configurations are not intended to limit application of the invention to any particular type of connector presently available or envisioned or yet to be developed. Moreover, end portions of tubes, according to some embodiments of the invention, are configured to mate with desired types of connectors. For example, in some embodiments, an inner or outer surface of an end portion of the tube is threaded to mate with a threaded connector.

As one illustrative example, convenient use of a tube with a standard connector is described with reference to FIG. 5.

Figure 5:
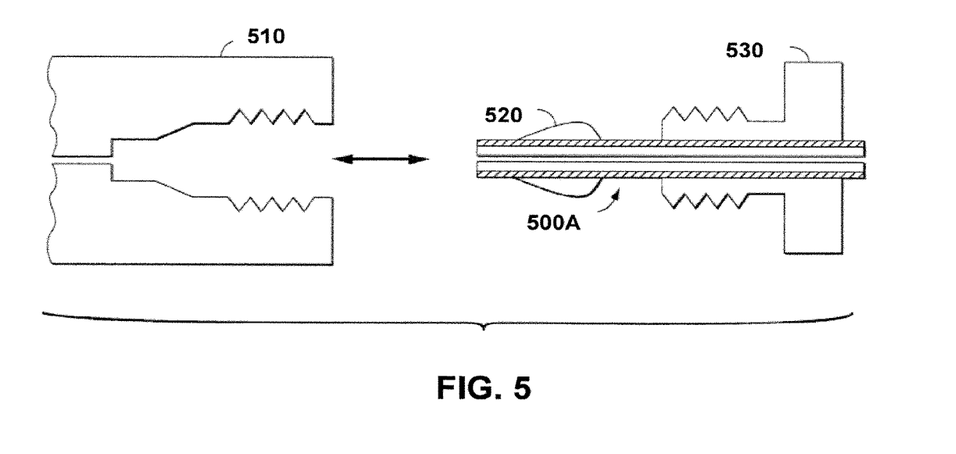
FIG. 5 is a cross-sectional diagram of a portion of a connector and a tube, in accordance with one embodiment of the invention.

FIG. 5 is a cross-sectional diagram that illustrates a portion of a chemical-processing apparatus, in accordance with one embodiment of the invention. The illustrated portion includes a conduit assembly 500A and conventional connector components 510, 520, 530. The connector components include a fitting body 510, a ferrule 520, and a fitting nut 530 (such as a compression screw.)

The conduit assembly 500A is, for example, fabricated according to the methods and/or has the structure of any of the embodiments described above with reference to FIGS. 1, 2a, 2b, 3, 4a and 4b. In particular, the conduit assembly has an outer tube that is selected for compatibility with the connector components 510, 520, 530. In the present example, the outer tube is formed from standard 1/16 inch OD stainless steel tubing.

A threaded portion of the fitting nut 530 mates with a threaded portion of the fitting body 510. The fitting nut 530, when tightened into the fitting body 510, compresses the ferrule 520 against the tube 500a to provide a seal against leaks.

Only a proximal end of the fitting body 510 is shown in FIG. 5. A distal end of the fitting body 510 has any desired configuration, including standard configurations. For example, the distal end may be configured as is the proximal end, i.e., to connect to a tube or a second conduit assembly. Alternatively, the distal end is attached to, or an integral part of, for example, an output port of a pump, an input port of a column, or a port of another component of an apparatus, such as a valve or flow splitter (see description below with reference to FIG. 6.) Thus, the connector is used, for example, to connect the conduit assembly 500A to another tube of similar or different OD, to a separation column, or to another component of an analytical instrument.

In view of the above description, one having ordinary skill in the separation arts will understand that conduit assemblies are optionally used in conjunction with any suitable connectors, including known connectors. One suitable commercially available connector, which includes a fitting, ferrule, and compression screw, is the SLIPFREE® connector (available from Waters Corporation, Milford, Mass.)

In view of the description contained herein, it will be apparent to one of ordinary skill that many other connectors are usable with various assembly embodiments. For example, some suitable connectors utilize a two-ferrule system. Such connectors have applications, for example, in high-pressure environments, for example, at pressures up to about 15,000 psi and greater.

One example of a connector that is suitable for use at very high pressure is the Swagelok gaugeable SAF 2507 super duplex tube fitting (available from the Swagelok Company, Solon, Ohio.) This connector includes front and back ferrules formed from different steel alloys. The back ferrule drives the front ferrule into a fitting body and onto the surface of a tube, to create a seal.

Figure 6:
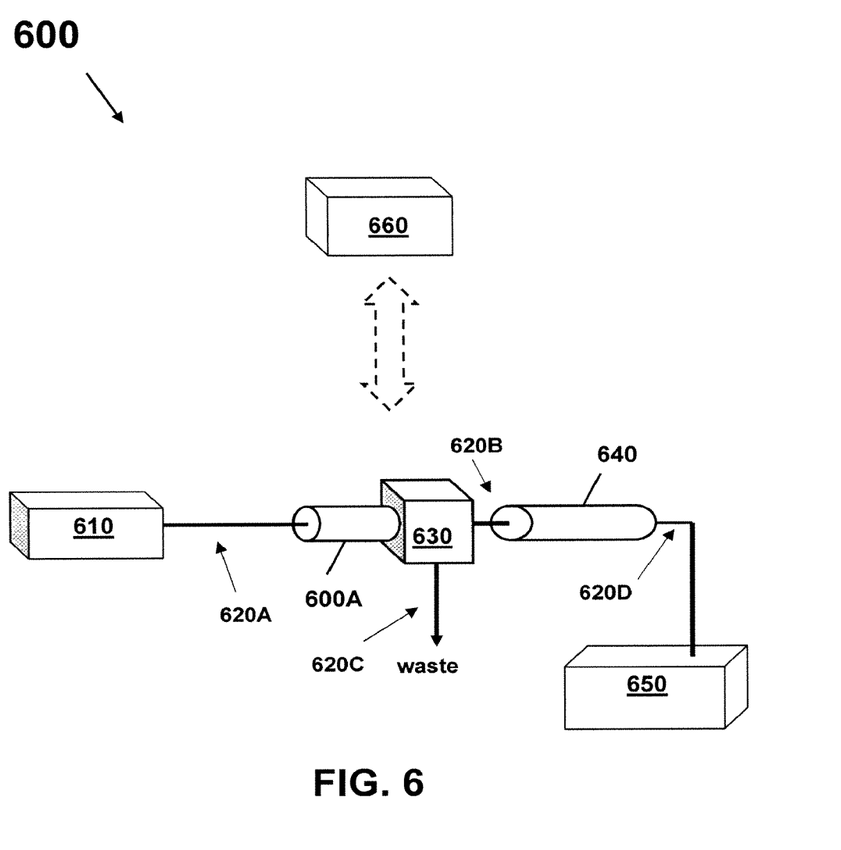
FIG. 6 is a block diagram of an analytical apparatus, in accordance with one embodiment of the invention.

FIG. 6 is a block diagram of a chromatography apparatus 600, such as a nano-flow LC apparatus, in accordance with another embodiment of the invention. The apparatus 600 includes a fluid-delivery component 610 (including, for example, solvent reservoir(s), a solvent pump(s), and a sample injector) a trap column assembly 600A, a separation column 640, a tee 630 to direct flow to waste and/or the separation column 640, a detector 650, tubing 620A, 620B, 620C, 620D connecting the various components of the apparatus 600, and a control module 660.

The trap column assembly 600A is directly attached to an input port of the tee 630. The tee 630 is any suitable tee, including commercially available tees such as a nano-tee available from Waters Corporation, Milford, Mass.

The trap column assembly 600A has a structure similar to that of the assembly 100 illustrated in FIG. 1 (with, however, the larger ID liner tube 131 containing a packing material.) The assembly 600A does not employ a second liner tube of smaller ID. Thus, the outlet end of the trap column (corresponding to the left-hand end of the liner tube 131 in FIG. 1) is flush with one end of the assembly 600A. Thus, the outlet of the trap column is directly mated to the tee 630.

The tubing 620A, 620B, 620C, 620D optionally has desired inner diameters that are appropriate for nano-flow chromatography, within a range, for example, of about 20 μm to about 40 μm. Each section of the tubing 620A, 620B, 620C, 620D optionally has a different inner diameter, as desired.

In some alternative implementations, the apparatus 600 is based on a known high-pressure chromatographic instrument, though modified. One suitable commercially available instrument is the nanoACQUITY UPLC™ System (available from Waters Corporation, Milford, Mass.)

The control module 660—including, for example, a personal computer or workstation—receives data and/or provides control signals via wired and/or wireless communications to, for example, the fluid-delivery component 610 and/or the detector 650. The control module 660 supports, for example, automation of sample analyses. The control module 660, in various alternative embodiments, includes software, firmware, and/or hardware (e.g., such as an application-specific integrated circuit), and includes, if desired, a user interface.

The column 640 contains any suitable stationary medium. For example, the medium optionally contains any suitable medium for nano-flow chromatography, such as a particulate medium known to one of ordinary skill. Some suitable media include silica and hybrid sorbents having particle diameters in a range of approximately 1 μm to approximately 5 μm. Moreover, the column 640 optionally is fabricated according to principles of the invention described above.

In some embodiments, a particulate medium includes hybrid particles, as found, for example, in the BEH Technology Acquity UPLC™ 1.7 μm columns (available from Waters Corporation, Milford, Mass.) Other embodiments include larger particles, such as 3 μm or 5 μm particles. Some of these embodiments involve trap columns.

Suitable columns are up to 25 cm in length, or greater, and have inner diameters in a range of, for example 20 μm to 300 μm, for example, 75 μm, 100 μm or 150 μm.

A suitable solvent pump is configured, for example, to provide nano-flow of solvent at pressures of at least approximately 5,000 psi or 10,000 psi or greater. The pump unit includes any suitable pump components, including known pump components, such as those found in Acquity UPLC™ liquid chromatography instruments (available from Waters Corporation, Milford, Mass.)

The apparatus 600 is suitable for, for example, 200 mL/min to 100 µL/min flow-rate separations that provide relatively good sensitivity, resolution and reproducibility. Such separations are desirable, for example, for biomarker discovery and for proteomics applications for protein identification and characterization. Thus, for example, scientists are aided in their investigations of large protein populations or proteomes to identify and quantify proteins that are either up-regulated or down-regulated. Observed changes in protein expression, for example, may provide an indication of disease states. Identifying subtle changes can provide valuable information for drug development. The nano-flow separation also suitably supports subsequent mass spectrometric analysis.

In some embodiments of the invention, a separation column is fabricated in accordance with one of the above-described embodiments of a conduit assembly. Such separation columns have an inner diameter within a range of, for example, approximately 20 µm to approximately 300 µm, and are preferably packed with a suitable medium, such as any of the above-described media.

Figure 7:
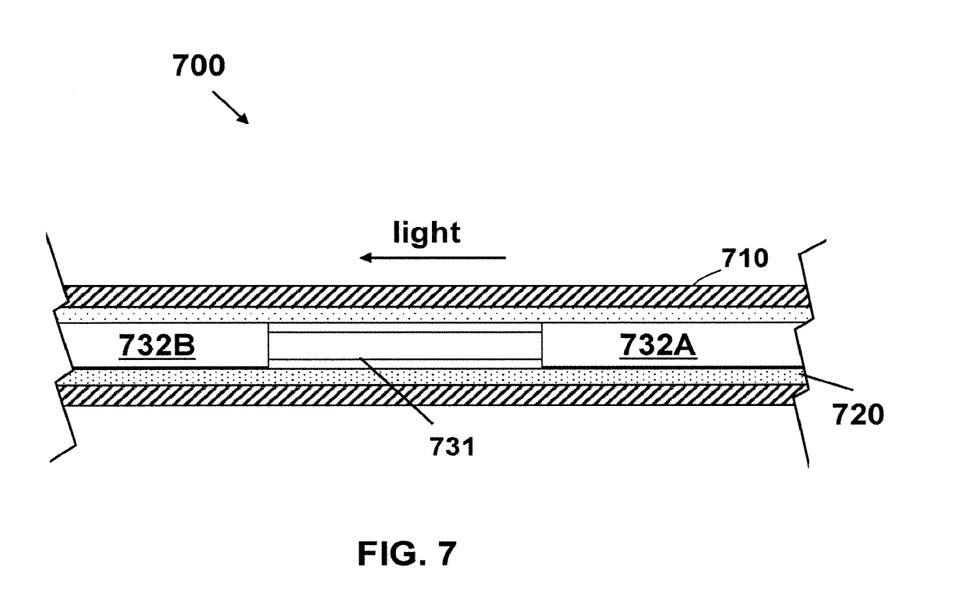
FIG. 7 is a cross-sectional diagram of a trap-column assembly, in accordance with one embodiment of the invention.

As noted above, one or more inner conduits are light conduits, in some embodiments of the invention. For example, FIG. 7 is a cross-sectional diagram of a flow-cell assembly 700, in accordance with one embodiment of the invention.

The assembly 700 includes an outer tube 710, an intermediate tube 720, two optical conduits 732A, 732B, and a liner tube 731 disposed between the two optical conduits 732A, 732B. In operation, the liner tube 731 contains a fluid for optical analysis. The assembly 700 optionally includes inlet and/or outlet port(s) to permit a fluid to flow into and/or out of the interior of the liner tube 731. Light is delivered to the fluid via one of the optical conduits 732A. Light emitted and/or transmitted by the fluid enters the other optical conduit 732B for delivery to a light detector. The flow-cell assembly 700 is optionally used for light-based analyses in a LC apparatus.

The liner tube 731 is formed of any suitable material(s), including known material(s). For example, the liner tube 731 is formed of a material that has optical properties that are suited to the functioning of a flow-cell based detector. The material suitably has a refractive index that is less than that of the liquid contained in the tube 731.

For example, the liner tube 731 optionally is formed of a fluoropolymer, such as TEFLON® amorphous fluoropolymer (available from E. I. du Pont de Nemours and Company, Wilmington, Del.) TEFLON® AF amorphous fluoropolymer is particularly well suited to flow-cell related embodiments of the invention.

Some embodiments utilize a mixture of a polymer and particles. For example, some embodiments utilize an amorphous fluoropolymer mixed with particles that block stray light. Suitable particles include, for example, carbon particles. One such suitable material is carbon-doped TEFLON® AF material ("black TEFLON® AF" material.) To prepare this material, TEFLON® AF resin is mixed, for example, with carbon black in a concentration range of 0.01%-0.1%.

As another alternative, the liner tube 731 is a fused-silica capillary having an outer surface coated with a lower refractive index material. In yet another example, the liner tube 731 has a highly reflective interior surface.

Alternative embodiments related to the assembly 700 dispense with the liner tube 731. In these embodiments, the intermediate tube 720 optionally supports the optical, chemical and/or physical properties that are desired for flow-cell functioning.

Figure 8A:
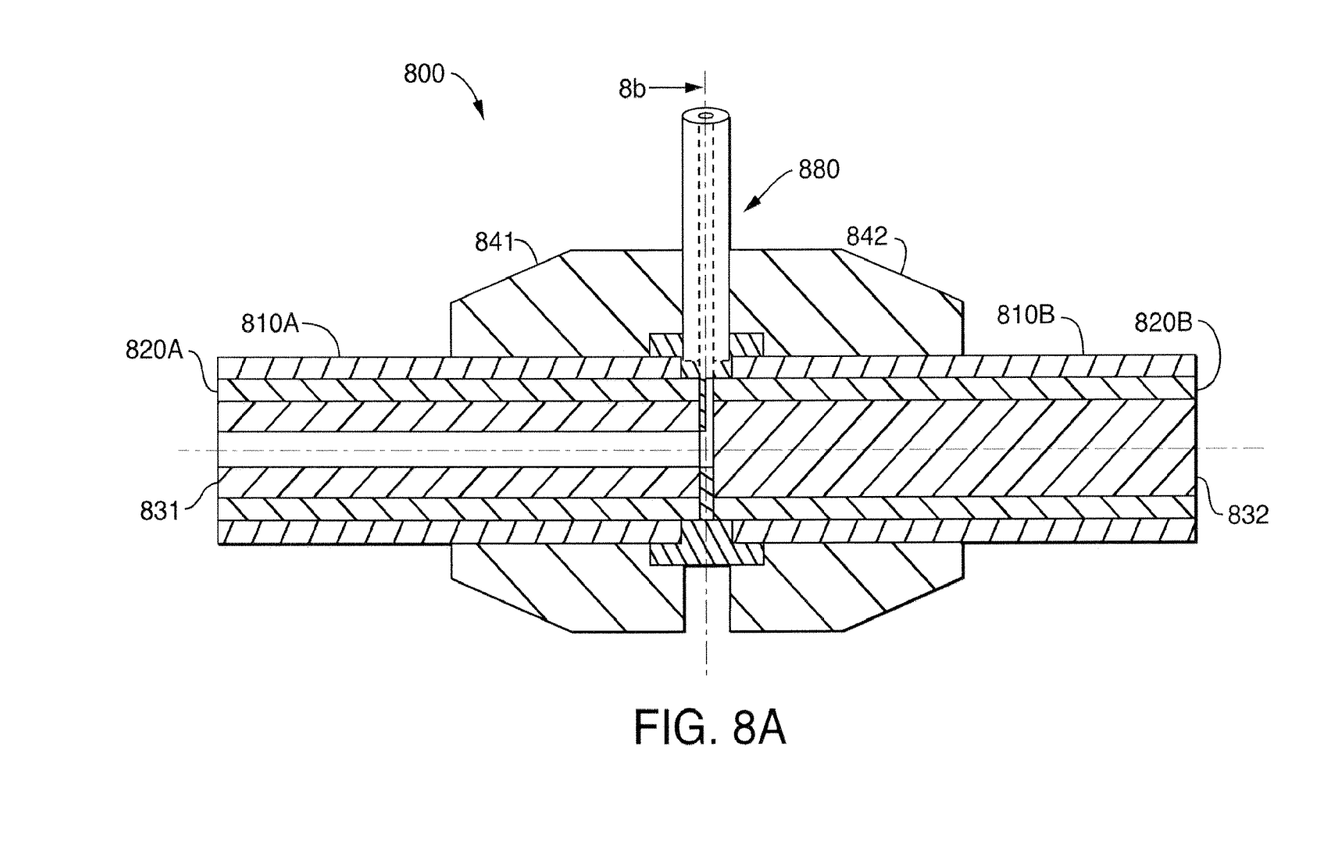
FIG. 8a is a cross-sectional diagram of one end of a flow-cell assembly including a fluidic-interface portion, in accordance with one embodiment of the invention.
Figure 8B:
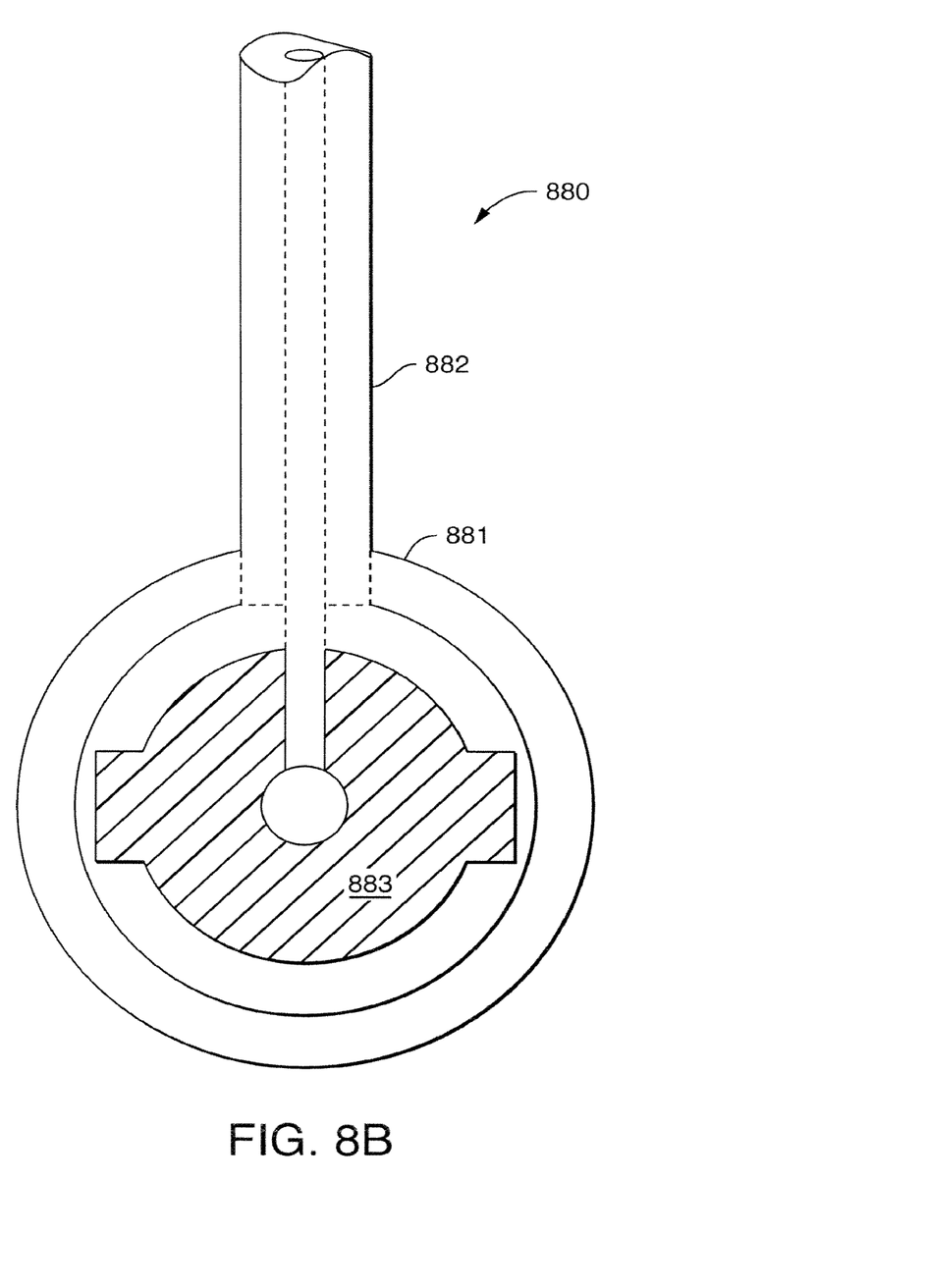

Next, as illustrated with reference to FIGS. 8a and 8b, some embodiments of the invention relate to flow cells, or other components, having one or more fluidic interfaces. For example, FIG. 8a is a cross-sectional diagram of one end of a flow-cell assembly 800, in accordance with one embodiment of the invention. The flow-cell assembly 800 includes two outer tubes 810A, 810B, two intermediate tubes 820A, 820B, an optical conduit 832, a liner tube 831, and a fluidic-interface assembly 880. In operation, the liner tube 831 contains a fluid, which can flow into and/or out of the liner tube 831 via the fluidic-interface assembly 880. The flow-cell assembly 800 optionally includes additional fluidic interfaces at, for example, an opposite end of the liner tube 831 and/or at intermediate locations along the flow-cell chamber defined by the liner tube 831.

The fluidic-interface assembly 880 includes a fitting 881, a tube 882 attached to or integrally formed with the fitting 881, and a spacer 883 disposed in, or integral to, the fitting 881. The tube 882 is attached to the fitting 881 via, for example, welding or brazing. As shown, the spacer 883 optionally includes registration features that correspond to recesses in the fitting 881. The spacer 883 is fabricated via, for example, chemical etching of laser machining.

The assembly 800 also includes fittings 841, 842, that are similar in construction to, for example, the above-described metal ferrules. The fittings 841, 842 are crimped to provide fluidic seals proximal to the interface defined by the liner tube 831 and the optical conduit 832. Similar to the above-description, the assembly 800 includes one or more distal seals.

A lumen defined within the tube 882 is aligned with a fluid passageway within the fitting 881. Similarly, the fluid passageway of the fitting 881 is aligned with a fluid passageway of the spacer 883. Thus, the assembly 880 provides a fluidic passage in communication with a fluid in the liner tube 831.

The fitting 881 has two circular bores that receive the outer tubes 810A, 810B. The fitting 881 is optionally sealed to the outer tubes 810A, 810B via, for example, welding or brazing, to provide leak-tightness. The two intermediate tubes 820A, 820B, the optical conduit 832, and the liner tube 831 are disposed in contact with the spacer 883 of the fluidic-interface assembly 880.

In operation, light travels along the optical conduit 832 and enters a fluid in the liner tube 831 after passing through an aperture defined by the spacer 833. The spacer 833 also serves to block light from entering the intermediate tube 820A. Light transmitted and/or emitted by the fluid is then detected after exiting the liner tube 831. Light optionally exits the tube 831 via a side of and/or end of the liner tube 831.

For example, an exit end of the tube 831 optionally is terminated with an optical window. For example, a cell the light exits may consist The assembly 800 optionally includes a second fluidic-interface assembly that terminates an opposite end of the liner tube 831. The first 880 and/or second fluidic-interface optionally include optical window(s).

An optical window, in some alternatives, is sealed to the end of the liner tube 831 via brazing or welding, use of O-rings, or any other suitable technique.

Some alternatives to flow-cell embodiments include fluidic interfaces. For example, one embodiment is a fluidic tee, in which two liner tubes having same or different diameters each receive fluid from a lumen of a fluidic interface.

Variations, modifications, and other implementations of what is described herein will occur to those of ordinary skill in the art without departing from the spirit and the scope of the invention as claimed. For example, though the embodiments of tubes illustrated herein have circular cross sections, the invention encompasses tubes that have non-circular cross sections. Moreover, for example, an assembly optionally includes two or more conduit interfaces, and the associated conduits optionally have two or more different inner diameters or different lumen shapes. Accordingly, the invention is to be defined not by the preceding illustrative description but instead by the spirit and scope of the following claims.

What is claimed is:

1. A liquid-chromatography apparatus, comprising:
   two inner conduits disposed end-to-end, in contact, to define a low dead-volume interface;
   an intermediate tube, within which the two inner conduits are disposed, wherein the intermediate tube is attached to at least one of the two inner conduits at a distal seal area spaced from the interface;
   an outer tube, within which the intermediate tube is disposed, wherein the outer tube is deformed at a location more proximal to the interface than the distal seal area such that is presses the intermediate tube against one of the inner conduits to form a substantially liquid-tight seal area between the inner conduit and the intermediate tube;
   wherein the distal seal area is larger than the substantially liquid-tight seal area and wherein the distal seal area substantially prevents the inner conduit from sliding within the intermediate tube during pressure cycling.

2. The apparatus of claim 1, wherein the two inner conduits comprise two liner tubes having different inner diameters.

3. The apparatus of claim 2, further comprising particles packed in the liner tube having a larger inner diameter.

4. The apparatus of claim 3, wherein the liner tube having the larger inner diameter defines a trap column or a separation column.

5. The apparatus of claim 4, further comprising a connector directly attached to an exit end of the trap column or the separation column.

6. The apparatus of claim 1, further comprising at least one ferrule disposed about the outer tube adjacent to the interface, and crimped to define the substantially liquid-tight seal area.

7. The apparatus of claim 1, further comprising a chemical frit disposed at the interface.

8. The apparatus of claim 1, wherein the two inner conduits comprise a tube and an optical conduit.

9. The apparatus of claim 8, wherein the optical conduit comprises at least one optical fiber.

10. The apparatus of claim 1, wherein at least one of the inner conduits comprises a fused silica tube.

11. The apparatus of claim 1, wherein the outer tube is deformed at a second location more proximal to the interface than the distal seal area such that it presses the intermediate tube against the other one of the inner conduits to form a second substantially liquid-tight seal area between the other one of the inner conduits and the intermediate tube.

12. The apparatus of claim 1, wherein the intermediate tube is attached to at least one of the inner conduits at the distal seal area by adhesion.

13. The apparatus of claim 12, wherein the intermediate tube is adhered to at least one of the inner conduits at the distal seal area by melt-bonding.

14. The apparatus of claim 13, wherein the distal seal area is at least about 1.0 cm from the interface.

15. The apparatus of claim 1, wherein the substantially liquid-tight seal area between the inner conduit and the intermediate tube is substantially liquid-tight to a pressure of greater than about 10 kpsi.

16. The apparatus of claim 1, wherein the intermediate tube is formed of a polymeric material.

17. The apparatus of claim 1, wherein the outer tube is formed of a material having a greater yield strength than a material that forms the intermediate tube.

18. The apparatus of claim 1, wherein the outer tube is formed of a metal.

* * * * *